United States Patent
Zhang

(10) Patent No.: US 9,968,481 B2
(45) Date of Patent: May 15, 2018

(54) USER FRIENDLY FEMALE CONDOM AND APPLICATOR

(71) Applicant: Wei Zhang, Sunnyvale, CA (US)

(72) Inventor: Wei Zhang, Sunnyvale, CA (US)

(*) Notice: Subject to any disclaimer, the term of this patent is extended or adjusted under 35 U.S.C. 154(b) by 286 days.

(21) Appl. No.: 14/658,037

(22) Filed: Mar. 13, 2015

(65) Prior Publication Data
US 2015/0359661 A1    Dec. 17, 2015

Related U.S. Application Data

(60) Provisional application No. 61/952,875, filed on Mar. 14, 2014.

(51) Int. Cl.
*A61F 6/06* (2006.01)
*A61F 6/00* (2006.01)

(52) U.S. Cl.
CPC .............. *A61F 6/005* (2013.01); *A61F 6/065* (2013.01)

(58) Field of Classification Search
CPC ...... A61F 6/005; A61F 6/04; A61F 2006/041; A61F 6/06; A61F 6/065; A61F 6/12
USPC ........................................ 128/830, 838, 840
See application file for complete search history.

(56) References Cited

U.S. PATENT DOCUMENTS

| | | | | |
|---|---|---|---|---|
| 4,805,604 A * | 2/1989 | Spery | ..... | A61F 6/065 128/830 |
| 4,840,624 A * | 6/1989 | Lee | ..... | A61F 6/065 604/349 |
| 4,867,176 A * | 9/1989 | Lash | ..... | A61F 6/065 128/830 |
| 4,945,923 A * | 8/1990 | Evans | ..... | A61F 6/065 128/837 |
| 5,433,219 A * | 7/1995 | Spery | ..... | A61F 6/065 128/844 |
| 2004/0054317 A1* | 3/2004 | Lemay | ..... | A61F 13/26 604/15 |

FOREIGN PATENT DOCUMENTS

GB    2454945 A  *  5/2009  ............... A61F 6/00

* cited by examiner

*Primary Examiner* — Kristen Matter

(57) ABSTRACT

We have developed a female condom and applicator apparatus that makes female condom easier to apply and more comfortable to use throughout the entire process. Several embodiments take advantage of traditional female tampon applicator structure and existing female condom design. This is easier for female users to adopt due to their already familiarity with similar device and their usage. One design has the applicator on the inside of the female condom which makes the applicator reusable. Another design has the entire female condom tucked inside the applicator, with the condom inner ring inside the applicator outer tube and condom outer ring inside applicator's inner ring. Another design has strings attached to the condom outside ring to keep it from moving or make noise. The device provides a low cost, easy to use, no side-effects, and ready-for-mass adoption solution for the market.

6 Claims, 8 Drawing Sheets

USER FRIENDLY FEMALE CONDOM AND APPLICATOR

CROSS REFERENCE OF RELATED APPLICATIONS

The present application claims the benefit of U.S. Provisional Application No. 61/952,875, filed on Mar. 14, 2014 entitled "User Friendly Female Condom", which is hereby incorporated by reference in its entirety.

STATEMENT REGARDING FEDERALLY SPONSORED RESEARCH OR DEVELOPMENT

None.

BACKGROUND OF THE INVENTIONS

This invention relates generally to female condoms and applicator, and more specifically, a user friendly female condom and applicator that make female condoms more comfortable and easier to use.

Condoms provide many benefits, such as preventing sexually transmitted diseases (STDs). Getting STDs is a risk that people face when they engage in intimate relationships. Some STDs, such as HIV, could be deadly. HIV is a virus that causes AIDS (acquired immunodeficiency syndrome). It is one of the world's most serious health issues. Since its first report in 1981, today an estimated 35 million people in the world currently live with HIV and tens of millions have died of AIDS. Among the infected HIV patients, 52% are women. Young women are twice likely to become infected with HIV than their male counterparts. Other STDs include genital herpes, viral hepatitis, bacterial vaginitis, pelvic inflammatory disease, syphilis, and etc. Some STDs are deadly, others causes serious health issues and discomforts. Therefore, it is highly advisable to take all necessary precaution to prevent STDs. Wearing condoms is one of the most effective and low cost approaches.

In addition, condoms are useful to prevent unplanned pregnancies. Couples may want to have an intimate relationship while avoid having children due to various reasons. Male condoms or female condoms are one of the effective ways to enable such outcome.

Whether one's ultimate goal is AIDS prevention, avoiding other sexually transmitted deceases, or reducing probability of pregnancy, condom is an effective tool because it is low cost and easy to use without any need of special training. We are focusing on improving female condom due to its huge untapped market with great potential of wide adoption. Women traditionally have higher stakes after pregnancy and thus generally have keener interests in birth controls. By targeting the more receptive stakeholders within female population, our effort can generate more significant impact on increasing condom adoption.

However, female condom has not gained expected traction, partly due to the difficulty of putting it on, especially during the first few uses. Female condoms comprises of two rings at each end of a cylindrical flexible tube having one end open. One ring is intended to stay inside the woman's vagina and another to stay outside during intercourse. Both inside and outside rings have to be large enough in diameter such that the inside rings does not come off easily during sexual intercourse, while the outside ring keeps the condom from being pushed inside the vagina. For such type of female condoms, one has to first squeeze the inside ring into an oval shape and then push fingers deep inside the condom tube in order to fully secure the condom into the vagina area. Many women don't feel comfortable inserting their fingers into their own vagina, either due to culture reasons or physical inconvenience/discomfort. In addition, other problems with female condoms include 1) the female condoms are made from opaque material which stands out from the skin color which might make female or her partner uncomfortable; 2) the out ring of the female condom is too thick, too hard and is an obvious prominent object in the genitalia area which also make the female or her partner uncomfortable; 3) the exposed part of the female condom is not attached to the skin which occasionally could cause the penis inserting into the outside wall of the female condom and causing failure in sexual decease or pregnancy prevention. Therefore, it is desirable to come up with a mechanism which enables placement of female condom easily and comfortably, preferably in a manner that is not frowned upon culturally.

BRIEF SUMMARY OF THE INVENTION

The following are four exemplary embodiments of a user friendly female condom and applicator device for the purpose of making it easier to apply and use female condoms. 1) The first design is named Sliding Tampon Female Condom which comprises of a tampon applicator-like structure or an outer tube made from a soft material capable of sliding back and forth easily on an inner tube/stick, placed insides a female condom. A portion of the Female Condom's inside ring, with or without a small portion of the Female Condom skin, are tucked inside the outer tube and then the device delivers the female condom into a woman's vagina comfortably without requiring her to insert her finger into her vagina. 2) The second design is called Female Condom Tampon Applicator which comprises of a tampon applicator or tampon applicator-like structure with the inside ring of a female condom largely or completely tucked inside its outer tube where a portion or all of the outside ring of the female condom is tucked inside the inner tube. Users can insert the device similar to a regular tampon and delivers the female condom, by pushing the inner tube against the inner ring of the female condom similarly as pushing a regular tampon, into the user's vagina comfortably without requiring her to insert her finger into her vagina. 3) The third design is named String Condoms where camouflage strings are attached to the outside ring of the female condom attaching them to the skin firmly but comfortably to prevent outer ring of the female condom being too thick or move around, thus reducing condom movement or noise level during sexual intercourse. 4) The forth design category consists of various combinations among the first three designs to make both the condom insertion process comfortable as well as reducing/eliminating issues during intercourse, and thus improving user experience during the entire condom usage process from beginning to end.

Several of our designs take advantage of the traditional female tampon structure and modify it for the purpose of delivering female condom. The first and second design is a creative approach by leveraging two existing proven designs. The third design simply adds non-apparent strings to the female condom to enable thinner outer ring of the female condom. Such incremental approach takes less time from proto-type to mass market production and is easier for female users to adopt due to their already familiarity with similar devices and their usage.

We believe that our approach is more likely to gain great success by improving on female condom, compared to approaches of modifying male condom. The main reason is that a female condom affects both parties' sensitivity/pleasure much less compared to a male condom. Therefore, young male will not mind using it if their partner is interested in using it. More importantly, greater than 50% of male population age 60 or older starts to experience occasional loss of erection during sexual intercourse. Therefore, they are not inclined to use male condom to make it harder to maintain erection. However, such older male populations likely don't want more children and thus will be more willing to use female condom if the condom doesn't affect their sexual ability. Therefore, if a design makes woman want to wear female condoms, it is bound to yield a significant uptake in protected sex.

In addition, women generally are more concerned about the consequences of sexual relationships, and thus are more willing to pay attention to the protection measures. Females are shown to generally exhibit the following characteristics: 1) Women are believed to pay more attention to details, easier to accept new subjects, willing to train, and proactive in learning; 2) Due to the impact of sexual relationship to women's own future and health, woman is particularly vocal about pregnancy prevention; 3) Female condom has more advantages than male condom because it has less impact on sensitivity.

The present invention advantageously fills the aforementioned deficiencies by providing an effective, comfortable, easy to use, and low cost device with no side effects to help prevent STDs.

In one particular embodiment of the present invention as shown in FIG. 1, the Sliding Tampon comprises a soft balloon (an air or liquid sac) surrounding a flexible tube (e.g. a silicon plastic tube). Alternatively, Sliding Tampon could simply be made of a regular tampon applicator tampon applicator-like structure. Sliding Tampon is placed inside a female condom with condom's inside ring tucked inside the balloon ahead of the tube. After inserting the Sliding Tampon applicator inside vagina similar to a regular tampon, by pushing the inside tube slowly and gently, the inside ring slides out of the balloon and is deposited into the vagina, then the balloon can be removed leaving the condom behind. The tube can be solid or made hollow so that regular or pressured air can be fed into the condom if needed.

We have developed a sample proto-type as show in FIG. 2. Since the balloon never touches female's skin, it enables re-use of the Sliding Tampon and thus is lower cost and more economical.

In another embodiment of the present invention, the device comprises tucking the entire female condom inside the soft balloon or tampon applicator-like structure to deliver the condom into vagina. Instead of just tucking the inside ring of the female condom into the balloon while the condom wall surrounds the balloon, the female condom inside ring with the surrounding condom skin is folded and bent into a slim long column shape with the outer ring of the condom with its ski folded and bent into a slim long column shape. The column is inserted into and encapsulated by the outer tube of a tampon application (or similar structure) (or the air or liquid balloon sac) largely or completely, with the outer ring largely or completely encapsulated by the inner tube of the tampon applicator (or similar structure). The tampon applicator (or like structure) is then placed in an orientation such that the inside ring of the condom would pop out first when the column's bottom is pushed outside the balloon.

In still another embodiment of the present invention, the female condom is attached to strings so that the outside ring of the condom does not dangle freely. The strings could be made from soft transparent or camouflage color such as skin color to make them less visible to the eye, yet comfortable to the skin. One can also combine this embodiments with the one or more of the previously mentioned embodiments.

It is therefore an object of the present invention to enable a female condom to be inserted easily and comfortably, while pleasant and convenient before, during, and after the condom usage for the female and her partner so that they want to adopt the usage of the female condom during their intimate sexual intercourse. The advantage of the present invention is that it is convenient and easy to use, low cost, and can be put on way ahead of the sexual intercourse. Compared with the female condoms sold on the market today, the device from the present invention is easier to put on, more comfortable during the sexual intercourse, and offers longer term benefits by enabling more female and male liking the usage of this device.

The present invention now will be described more fully hereinafter with reference to accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

BRIEF DESCRIPTION OF THE SEVERAL VIEWS OF THE DRAWINGS

The invention may take physical form in certain parts and arrangement of parts, a preferred embodiment of which will be described in detail in this specification and illustrated in the accompanying drawings which form a part hereof and wherein.

DETAILED DESCRIPTION OF THE INVENTION

The present invention is directed to a user friendly female condom that is low cost, easy to put on, comfortable to wear, convenient for the female user and her partner.

Figure 1:
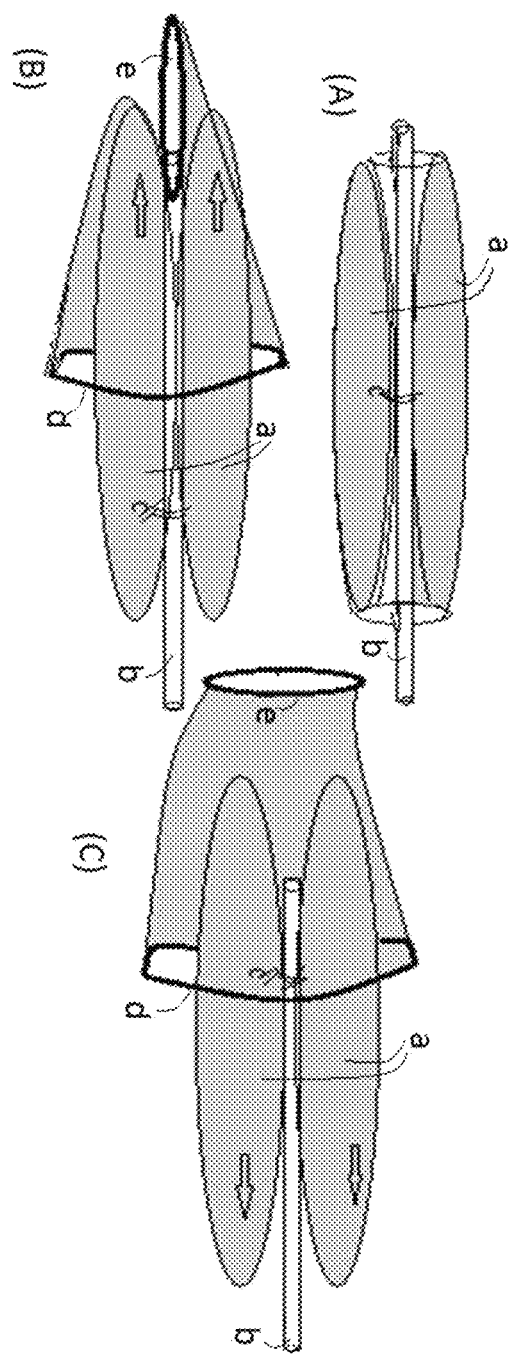
FIG. 1 is a view in perspective of sliding tampon female condom comprised of a balloon sac filled with air or liquid, with the female condom bottom ring inserted into the middle of the balloon while the condom wall enwraps the balloon, in accordance with one or more implementations.

Referring now to the drawings wherein the showings are for purposes of illustrating a preferred embodiment of the invention only and not for purposes of limiting the same, FIG. 1(A) shows a sliding tampon female condom. The device comprises a balloon sac, a, filled with liquid or air. The balloon sac enwraps a tube, b, which could be made of somewhat flexible material such as silicon or plastic. The tube can be made into solid material or hollow shape. The advantage of the hollow shape is that it allows air to be pumped into or drawn out of the condom through the tube. FIG. 1(A) depicts a liquid balloon made from a liquid rectangle shape folded into a cylinder and sewed to stay as a cylinder by ligated silk, c. FIG. 1(B) illustrates the process of delivering the female condom into a woman's vagina. First of all, the bottom portion of the balloon a needs to be put into the female condom through the outer ring d while the inside ring e of the female condom is squeezed into an elongated oval shape and tucked into the bottom center of the balloon sac. The inside ring pushes the tube b inside the balloon up toward the top portion of the balloon while the balloon slides down to encapsulate the inside ring. Then, the female user can hold the top portion of the balloon including the tube; slowly and smoothly insert the entire unit into her vagina. The balloon is longer than the woman's vagina so that after the entire unit is inserted into the vagina, the outer ring and the top of the balloon where the finger is holding are still comfortably outside the vagina. In FIG. 1(C), the user slowly and gently pushes the tube which could be accomplished alternatively or complimentarily by pumping air via the hollow tube into the condom. This will push the tucked inside ring e out of the balloon a and pop it into the bottom chamber of the vagina, securing the female condom into the vagina. Then the balloon can be pulled out together with the tube, leaving the female condom behind. Because the balloon is filled with air or liquid, it does not cause discomfort when inserting the entire unit into the vagina. The user uses the balloon aided with the tube to deliver the inside ring into the bottom chamber of the vagina, so she doesn't have to push her finger(s) into her vagina. This is very similar to the usage of a tampon and thus is more acceptable to culturally conservative countries.

Figure 2:
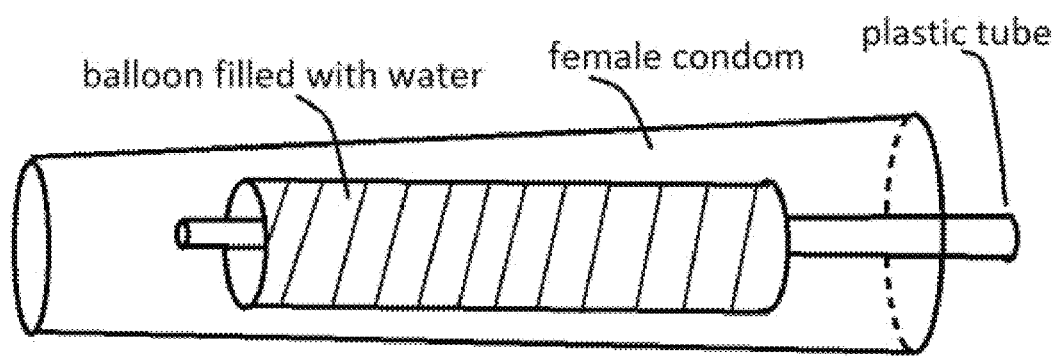
FIG. 2 is a picture of the prototype liquid balloon enwrapped inside a female condom, in accordance with one or more implementations.

FIG. 2 is a prototype of the sliding tampon female condom. The balloon was made from a regular balloon filled with water. The tube is a plastic hollow tube. There are many low cost ways to make a liquid balloon sac. This prototype was made with regular Banner balloons. Flip the bottom of a long banner balloon inside out so that the bottom of the balloon sticks out of the balloon's top from the inside and the balloon has double walls. Fill water between the two walls. Cut the bottom of the balloon that sticks out of the balloon top. Then seal the two walls together with super-glue or other method in the top so they are water-tight. A 16 cm long plastic tube is inserted into the middle of the double walled balloon. The water in the balloon is fluidic and smooth; therefore is comfortable and causes no pain.

Figure 3A:
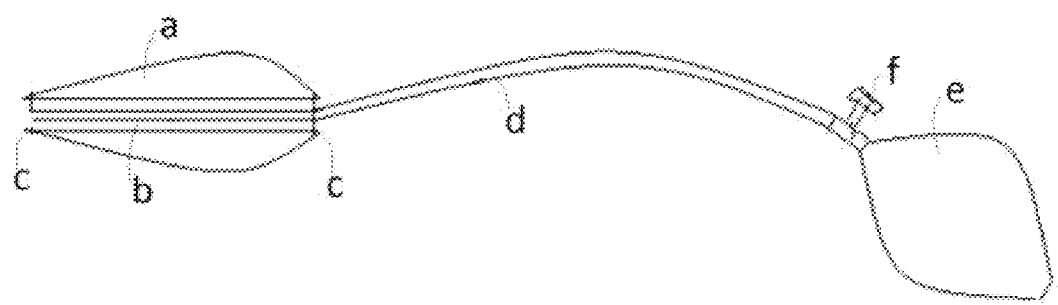
FIG. 3 is a perspective view of the balloon sac connected with a rubber air ball for pushing and drawing air through the plastic tube inside the balloon, in accordance with one or more implementations.
Figure 3B:
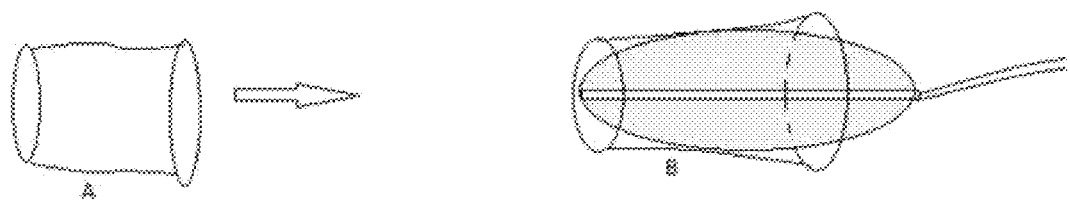

FIG. 3 demonstrates how to use an air pump through the tube to aid the condom insertion process. In FIG. 3(a), balloon sac a is filled with air and enwraps a small plastic tube b, while a silk thread tie, c, at the top of the air balloon prevents air from leaking. In addition, a soft plastic tube connects the small plastic tube with a rubber air ball pump, e, controlled by a switch, f. When the switch f is turned on, e pumps air through soft tube d via plastic tube b into the bottom portion of the air balloon sac. As shown in FIG. 3(b), a female condom A is put onto the air balloon sac one unit of B. Not shown in the figure is that the bottom inside ring of the condom is squeezed into oval shape and tucked into the bottom inside of the air balloon sac. Then unit B is delivered into the woman's vagina. After reaching the bottom of the vagina, the switch f is tuned on and the pump e will send high pressure air into the bottom of the air balloon sac, pushing the inside ring out of the balloon sac and depositing the inside ring at the bottom chamber of the vagina. In this embodiment, the balloon sac never touches the vagina and therefore can be used multiple times if the user chooses to do so, therefore decreasing the overall cost even further.

Figure 4A:
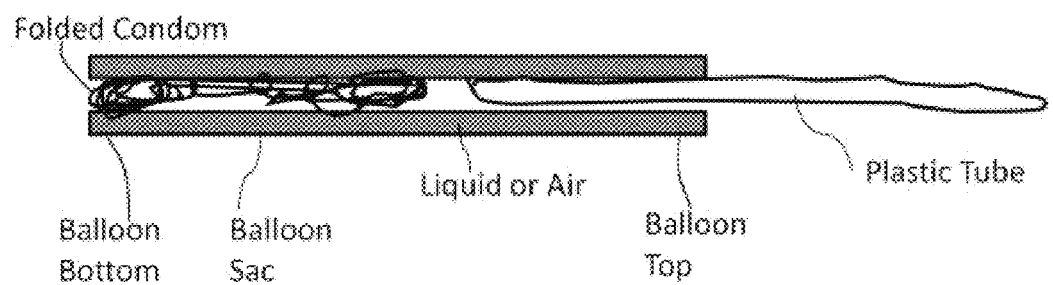
FIG. 4 is the cross sectional view of a female condom wrapped into a column inserted completely inside a balloon sac, in accordance with one or more implementations.

FIG. 4(a) explains another embodiment of delivering a condom easily into the vagina. A long cylindrically shaped balloon sac enwraps a plastic tube which has a length equal to or slightly longer than that of the balloon. The balloon sac could be filled with liquid or air. Alternatively the long cylinder could be the outer tube of a tampon applicator. A female condom is folded into a small elongated column shape and inserted from the bottom portion of a balloon sac into the center portion of the balloon sac or from back of a tampon applicator outer tube and pushed toward the front of the tube. The folded condom pushes a portion of the plastic tube out of the balloon. Alternatively, the outer ring of the condom is folded/bend into an elongated column and pushed through the inner tube of the tampon applicator (not shown in the figure). The folded condom is folded and oriented such that its inside ring sits at the bottom portion of the balloon bottom. The whole unit can then be inserted into a user's vagina by holding the balloon top portion. After reaching the bottom of the vagina, the tube is slowly and smoothly pushed toward the balloon bottom, pushing the inside ring out of the bottom of the balloon, which will pop into the bottom chamber of the vagina, the tube can then be slowly pulled out of the vagina, with the inside ring holding the entire condom in the vagina. Since the condom is much longer than the vagina, the outer ring will be left outside the vagina. Thus, the whole process is smoothly, comfortable, without inserting the finger into one's vagina. This usage is very similar to tampon usage. After each use, the balloon needs to be thrown away and can't be reused.

Figure 4B:
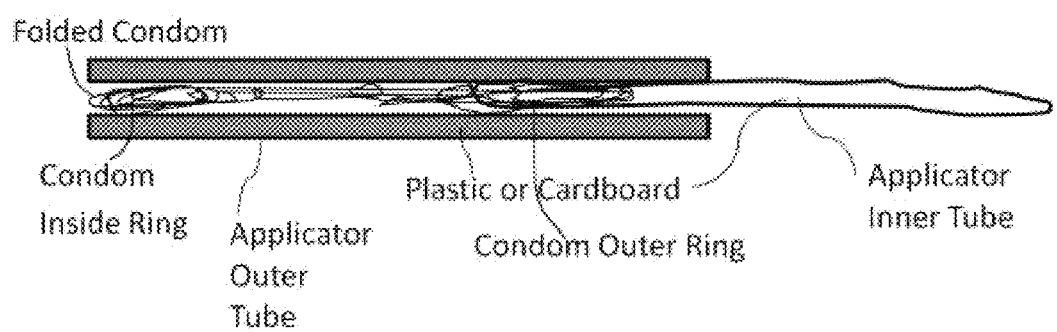

FIG. 4(b) depicts the case when the balloon sac is replaced with the out tube of a tampon applicator where the plastic tube is replaced with the inner tube of the tampon applicator.

Some people are uncomfortable with the large and hard out ring of the female condom. In addition, its dangling outside the vagina makes the woman feel unattractive. Therefore, we have designed a bikini-like condom or condom with strings to improve on this aspect.

Figure 5:
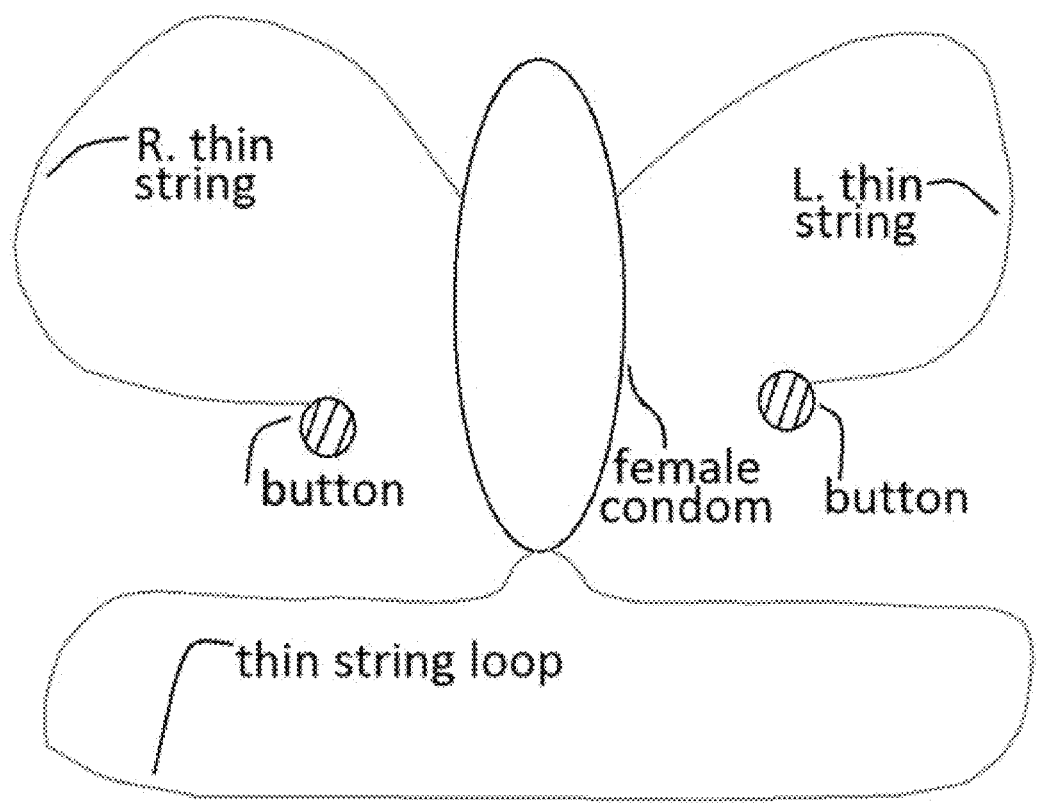
FIG. 5 is a picture of a prototype of a female condom with strings, in accordance with one or more implementations.

FIG. 5 is a prototype of the female condom with strings. A female condom without the outer ring may have a much softer outside edge, which could be in ring shape, star fish shape, square, flower pedal shape, heart shape, etc. The prototype here is a female condom with a simple soft outside ring. To prevent the condom getting pushing into the vagina during intercourse and avoid the outside ring dangling unattractively outside the vagina, a few transparent thin and comfortable to the skin strings are attached to the outside ring. In the upper left is a string for right thigh, labeled as R. thin string, with a button at the end. Of course, this button can be replaced with other ways to connect or secure the strings. In the upper right is a thin string for the left thigh, labeled as L. thin string, with a button at the end. At the bottom is a thin string loop.

Figure 6:
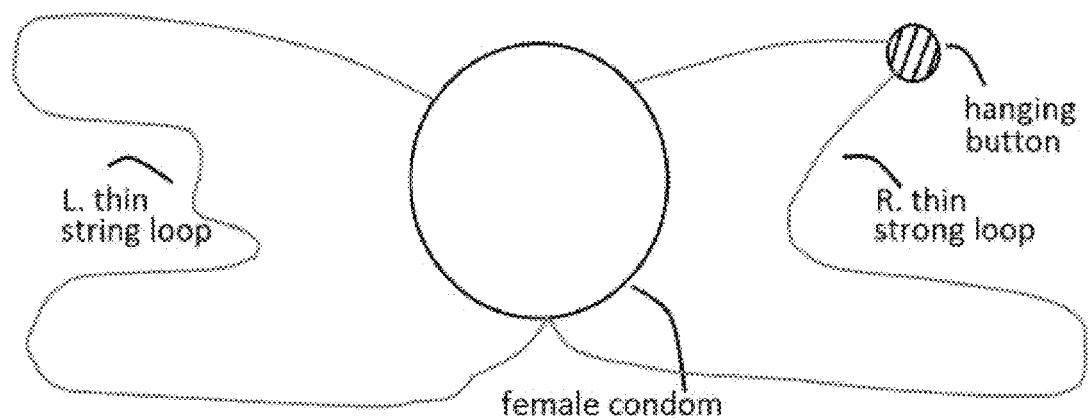
FIG. 6 is a picture of an alternative design in placing the strings on the female condom, in accordance with one or more implementations.

FIG. 6 is another design regarding where to place the strings. This embodiment simply had a right thin loop, a left thin loop, and a hanging button. One simply needs to put left thin loop through the left thigh and right thin loop through the right thigh. The left thin loop can be secured by looping through the hanging button in the back.

Another embodiment is a bikini-like condom to make the condom comfortable to wear and pleasant to look at by everyone. The condom can be worn anytime constantly. When the female needs to urinate, she only needs to open a small covering, which could be artistically designed, without removing the bikini-like condom.

Figure 7:
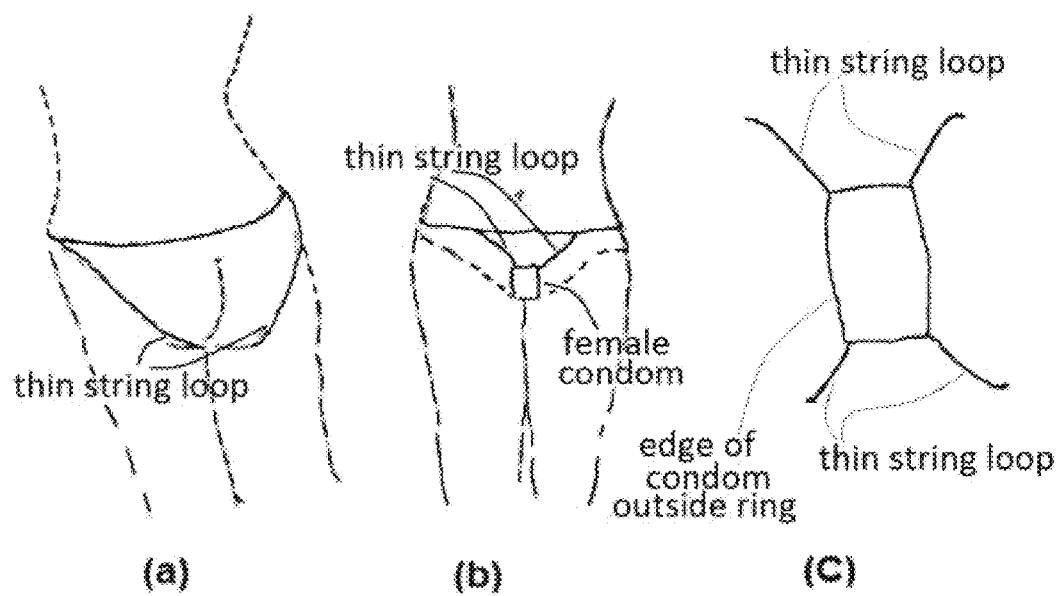
FIG. 7 is a perspective view of illustration of the female condom with strings or bikini-like condom and how it could be worn, in accordance with one or more implementations.

FIG. 7 illustrates a bikini-like female condom and how it works. FIG. 7(*a*) is the back view. As can be seen, dotted lines are the thin strings attached to the condom. In this case, there is a left thigh thin string and a right thigh thin string. In addition, there could be a waist line thin string to further secure the condom into place. FIG. 7(*b*) is the front view of the bikini-like condom. As shown by the dotted lines to represent the thin strings, there is a left thigh thin string, a right thigh thin string, and a waist thin string. FIG. 7(*c*) is a bottom view of the bikini-like condom worn by a user. In this case, the female condom has been put into the vagina while the thin left thigh and right thigh strings keep the outside soft edge of the female condom closely attached to the body so it is not flapping around unattractively. If the condom is made into skin color and conforms well to the body, with the thin string essentially invisible, it serves as an effective camouflage. In addition, in FIG. 7(*c*), the outside ring of the condom is shaped into a rectangle. However, this can be made into any other shapes, for either functional purposes or esthetical effects to please the eyes. For example, the outside edge can be a circle, an upside down heart, a star, a triangle, a flower, a pedal, a smiling face, etc. In one of the embodiments, the edge of the outside ring is made with elastic material so that it stretches smoothly into a relatively flat surface pulled by the strings. With such stretching material as the edge of the outside portion, a smiling face becomes a bigger smile, a circle might become an oval, a flower might become a disproportionate shape, etc., which could be fun and please to the user and her partner.

When the female user needs to go urinate, she can simply adjust the thin strings so that the soft outside ring is pulled forward toward the belly button more to expose the urethra to urinate without removing the bikini-like condom.

Figure 8:
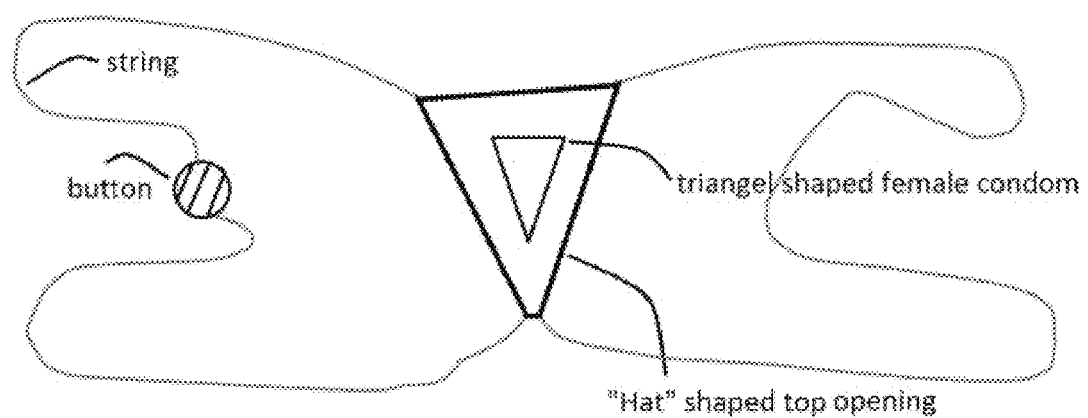
FIG. 8 is a picture of a prototype of a female condom with strings with the condom shaped like a hat, in accordance with one or more implementations.

FIG. 8 is another embodiment of the invention where the female condom is made into a triangle shape such that the cross section is a triangle rather than the typical circle. This makes the condom conform better to the shape of the genital triangle and much easier to attach to the body. The picture show the prototype of the transparent condom made into such triangle shape. There are one string loop on each side of the condom with a total three attached points to the condom. Each string loop attaches to the side on one end and jointly attach to the mid-point of the bottom edge of the outside ring. The way, the two strings on the front will fall into the groin area, passing through the iliac crest, then fall on gluteal sulcus, which enables good results of concealment.

While the present invention has been described above in terms of specific embodiments, it is to be understood that the invention is not limited to these disclosed embodiments. Many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

I claim:

1. A delivery device comprising:
   a female condom with an outer ring; and
   a cylindrically shaped object having first and second open ends, the object comprising a balloon filled with a liquid or gas, the outer ring of the condom being inserted into the object via one of the open ends;
   wherein the device is configured to deliver the condom inside a vagina by inserting the first end of the object into the vagina and removing the object, leaving the condom in the vagina.

2. The device of claim 1, wherein the condom further comprises an inner ring configured for placement inside the vagina.

3. The device of claim 1, wherein the entire condom is inserted inside the object.

4. The device of claim 1, wherein the condom further includes an inner ring; wherein the object comprises an inner tube and an outer tube; and wherein at least a portion of the inner ring is inserted into the outer tube and at least a portion of the outer ring is inserted into the inner tube.

5. A method for delivering a female condom, the method comprising:
   providing the female condom, the condom including an outer ring;
   inserting at least a portion of the outer ring into a cylindrically shaped object having first and second open ends, the object comprising a balloon filled with a liquid or gas; and
   delivering the condom inside a vagina by inserting the first end of the object into the vagina and removing the object, leaving the condom in the vagina.

6. The method of claim 5, wherein the condom further includes an inner ring; wherein the object comprises an inner tube and an outer tube; and wherein at least a portion of the inner ring is inserted into the outer tube and at least a portion of the outer ring is inserted into the inner tube.

* * * * *